(12) United States Patent
Meridew et al.

(10) Patent No.: US 7,670,343 B2
(45) Date of Patent: Mar. 2, 2010

(54) METHOD AND APPARATUS FOR REAMING AN ACETABULUM

(75) Inventors: Jason D Meridew, Syracuse, IN (US); Kim S Parcher, Etna Green, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 411 days.

(21) Appl. No.: 11/453,312

(22) Filed: Jun. 14, 2006

(65) Prior Publication Data

US 2008/0009874 A1 Jan. 10, 2008

(51) Int. Cl.
*A61B 17/00* (2006.01)
(52) U.S. Cl. .................................................. 606/81
(58) Field of Classification Search ............ 606/81, 606/96
See application file for complete search history.

(56) References Cited

U.S. PATENT DOCUMENTS

| | | | |
|---|---|---|---|
| 1,950,362 A * | 3/1934 | Manning | 81/414 |
| 3,744,061 A | 7/1973 | Frost | |
| 3,891,997 A | 7/1975 | Herbert | |
| 4,528,980 A | 7/1985 | Kenna | |
| 4,611,587 A | 9/1986 | Powlan | |
| 4,634,444 A | 1/1987 | Noiles | |
| 4,662,891 A | 5/1987 | Noiles | |
| 4,678,472 A | 7/1987 | Noiles | |
| 4,695,282 A | 9/1987 | Forte et al. | |
| 4,704,127 A | 11/1987 | Averill et al. | |
| 4,711,233 A | 12/1987 | Brown | |
| 4,712,951 A | 12/1987 | Brown | |
| D296,714 S | 7/1988 | Averill et al. | |
| 4,777,942 A | 10/1988 | Frey et al. | |
| 4,798,610 A | 1/1989 | Averill et al. | |
| 4,801,301 A | 1/1989 | Noiles | |
| 4,846,839 A | 7/1989 | Noiles | |
| 4,856,503 A | 8/1989 | Schelhas | |
| 4,865,603 A | 9/1989 | Noiles | |
| 4,871,368 A | 10/1989 | Wagner | |
| 4,883,491 A | 11/1989 | Mallory et al. | |
| 4,892,549 A | 1/1990 | Figgie, III et al. | |
| 4,944,759 A | 7/1990 | Mallory et al. | |
| 4,950,299 A | 8/1990 | Noiles | |
| 4,960,427 A | 10/1990 | Noiles | |

(Continued)

FOREIGN PATENT DOCUMENTS

CH 644 511 8/1984

(Continued)

*Primary Examiner*—Thomas C Barrett
*Assistant Examiner*—David W Bates
(74) *Attorney, Agent, or Firm*—Harness, Dickey (57) ABSTRACT

A method and apparatus for repairing a cavity in bone may can include a longitudinal shaft having a distal end and a proximal end. A cutting tool can be selectively attachable to the distal end. A one-piece guide can have a body defining an opening and including a locator member extending therefrom. The locator member can be engageable to a first portion of the bone providing a reference point relative to the cutting tool while the cutting tool engages a second portion of the bone during cutting. The body can be slidably advanced onto the longitudinal shaft through the opening from the proximal end to an operating location in an assembled position. During operation, the body can define a handle concentric with the longitudinal shaft.

20 Claims, 8 Drawing Sheets

U.S. PATENT DOCUMENTS

| | | |
|---|---|---|
| 4,963,154 A | 10/1990 | Anapliotis et al. |
| 4,978,356 A | 12/1990 | Noiles |
| 4,986,147 A * | 1/1991 | Cooper ....................... 81/63.2 |
| 5,021,063 A | 6/1991 | Tager |
| 5,030,219 A | 7/1991 | Matsen, III et al. |
| 5,100,409 A | 3/1992 | Coates et al. |
| 5,116,165 A | 5/1992 | Salyer |
| 5,176,710 A | 1/1993 | Hahn et al. |
| 5,176,711 A | 1/1993 | Grimes |
| 5,192,329 A | 3/1993 | Christie et al. |
| 5,282,864 A | 2/1994 | Noiles et al. |
| 5,290,315 A | 3/1994 | DeCarlo, Jr. |
| 5,312,411 A | 5/1994 | Steele et al. |
| 5,358,532 A | 10/1994 | Evans et al. |
| 5,370,704 A | 12/1994 | DeCarlo, Jr. |
| 5,413,603 A | 5/1995 | Noiles et al. |
| 5,437,677 A | 8/1995 | Shearer et al. |
| 5,468,243 A | 11/1995 | Halpern |
| 5,496,324 A | 3/1996 | Barnes |
| 5,549,694 A | 8/1996 | Noiles et al. |
| 5,549,697 A | 8/1996 | Caldarise |
| 5,549,698 A | 8/1996 | Averill et al. |
| 5,549,701 A | 8/1996 | Mikhail |
| 5,571,201 A | 11/1996 | Averill et al. |
| 5,624,447 A | 4/1997 | Myers |
| 5,669,915 A | 9/1997 | Caspar et al. |
| 5,676,704 A | 10/1997 | Ries et al. |
| 5,733,289 A | 3/1998 | Seedhom et al. |
| 5,769,856 A | 6/1998 | Dong et al. |
| 5,792,044 A * | 8/1998 | Foley et al. .................. 600/114 |
| 5,895,389 A | 4/1999 | Schenk et al. |
| 5,919,195 A * | 7/1999 | Wilson et al. ................. 606/80 |
| 5,928,288 A | 7/1999 | Wilson |
| 5,961,530 A | 10/1999 | Moore et al. |
| 5,976,145 A | 11/1999 | Kennefick, III |
| 6,102,915 A | 8/2000 | Bresler et al. |
| 6,245,074 B1 | 6/2001 | Allard et al. |
| 6,273,891 B1 | 8/2001 | Masini |
| 6,395,005 B1 | 5/2002 | Lovell |
| 6,416,553 B1 | 7/2002 | White et al. |
| 6,673,115 B2 | 1/2004 | Resch et al. |
| 6,682,567 B1 | 1/2004 | Schroeder |
| 6,702,822 B1 | 3/2004 | Noiles et al. |
| 6,875,218 B2 | 4/2005 | Dye et al. |

FOREIGN PATENT DOCUMENTS

| | | |
|---|---|---|
| DE | 3406357 | 12/1984 |
| EP | 0 091 315 | 7/1986 |
| EP | 0 309 363 | 3/1989 |
| EP | 0 205 132 | 10/1991 |
| EP | 0 303 006 | 3/1992 |
| FR | 2 516 377 | 5/1983 |
| GB | 1 409 051 | 10/1975 |
| SU | 1561975 | 5/1990 |
| SU | 1630799 | 2/1991 |

* cited by examiner

METHOD AND APPARATUS FOR REAMING AN ACETABULUM

FIELD

This invention relates generally to a method and apparatus for use in orthopedic surgery and, more particular, to a method and apparatus for positively positioning a tool while reaming an acetabular defect during orthopedic surgery.

BACKGROUND

A natural hip joint may undergo degenerative changes due to a variety of etiologies. When such degenerative changes become so far advanced and irreversible, it may ultimately become necessary to replace a natural hip joint with a prosthetic hip. If the acetabulum needs repair, all remnants of articular cartilage may be removed from the acetabulum and an acetabular prosthesis which will accommodate the head or ball of the hip prosthesis may be affixed to the acetabulum.

In some instances however, it may also be necessary to remove a defect located adjacent the acetabulum. It some cases, it may be difficult to accurately manipulate a tool such as a reamer at the defect. Sometimes the defect may be removed by hand instruments.

SUMMARY

An apparatus for repairing a cavity in bone can include a longitudinal shaft having a distal end and a proximal end. A cutting tool can be selectively attachable to the distal end. A one-piece guide can have a body defining an opening and including a locator member extending therefrom. The locator member can be engageable to a first portion of the bone providing a reference point relative to the cutting tool while the cutting tool engages a second portion of the bone during cutting. The body can be slidably advanced onto the longitudinal shaft through the opening from the proximal end to an operating location in an assembled position. During operation, the body can define a handle concentric with the longitudinal shaft.

According to additional features, the body can define an arm operably connected between the locator member and the body. The arm can define a first section arranged generally parallel to an axis defined by the longitudinal shaft and a second section arranged at an angle relative to the axis. A third section of the arm can be operably coupled between the locator member and the second section. The third section can be arranged generally parallel to the first section. The locator member can define a spherical outer engaging surface. The locator member can define a concave recess defined on an inner surface. The concave recess can accommodate the tool during operation.

A method for reaming a cavity in bone can include reaming an acetabular cavity with a reamer having a longitudinal shaft. A guide member can be attached to the longitudinal shaft. The guide member can be positioned in the reamed cavity thereby providing a reference point relative to the reamer. The guide member can define a handle concentric with the longitudinal shaft. The handle can be grasped with a first hand while the longitudinal shaft is grasped with a second hand. A defect adjacent to the reamed cavity can be reamed with the reamer.

Further areas of applicability of the present disclosure will become apparent from the detailed description provided hereinafter. It should be understood that the detailed description and various examples, while indicating various embodiments of the invention, are intended for purposes of illustration only and are not intended to limit the scope of the following claims.

BRIEF DESCRIPTION OF THE FIGURES

The present invention will become more fully understood from the detailed description and the accompanying drawings, wherein.

DETAILED DESCRIPTION OF VARIOUS EMBODIMENTS

The following description of various embodiment(s) is merely exemplary in nature and is in no way intended to limit the application or uses.

Figure 1:
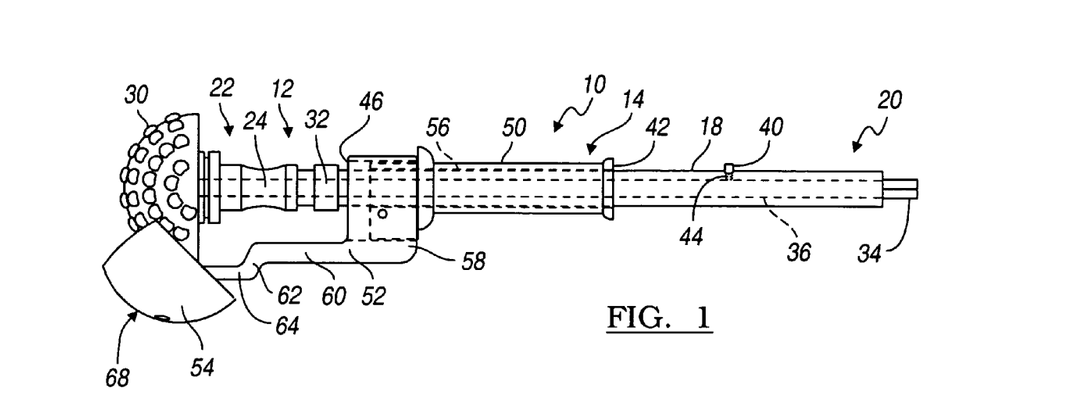
FIG. 1 is a side view of a tool having a reamer and a reamer guide according to the present teachings.

With initial reference to FIG. 1, a tool for reaming an area of an acetabulum is shown and generally identified at reference numeral 10. The tool 10 generally includes a reamer 12 and a guide member or reamer guide 14. As will become appreciated from the following description, the tool 10 may be used to ream an area of the acetabulum having a defect. More specifically, the reamer guide 14 may be used to positively locate or reference at a first location, such as within an acetabular cavity, while the reamer 12 is used to ream a second location, such as the defect.

With continued reference to FIG. 1, the reamer 12 will be described in greater detail. The reamer 12 may generally define a longitudinal shaft 18 having a proximal end and a distal end 20 and 22, respectively. The proximal end 20 may define mating structure 34 for coupling with a driver during operation. Such drivers may include pneumatic drivers, manual drivers or others. In one example, the driver may utilize a quick connect for securing at the mating structure 34. It is appreciated that the driver may impart rotational force onto the mating structure 34. The distal end 22 may include a mounting collar 24 defining attachment structure for selectively receiving a cutting head 30 thereat. A hub 32 may be formed near the distal end 22. The attachment structure may comprise any suitable mechanical coupling for securing the distal end 22 to the cutting head 30.

The rotational force of the driver may be communicated to the cutting head 30 by way of a reamer drive shaft 36 within the longitudinal shaft 18 operably connecting the mating structure 34 with the cutting head 30. A stop member 40 may be provided intermediate the proximal and distal ends 20 and 22. In one example, the stop member 40 may cooperate with the hub 32 to capture the reamer guide 14 therebetween during operation. As will be described in greater detail herein, the longitudinal shaft 18 of the reamer 12 may slidably translate through the reamer guide 14 in a first direction (leftward as viewed from FIG. 1) until the stopper 40 engages a proximal surface 42 of the reamer guide 14 and in a second direction (rightward as viewed from FIG. 1) until the hub 32 engages a distal surface 46 of the reamer guide 14.

Figure 4:
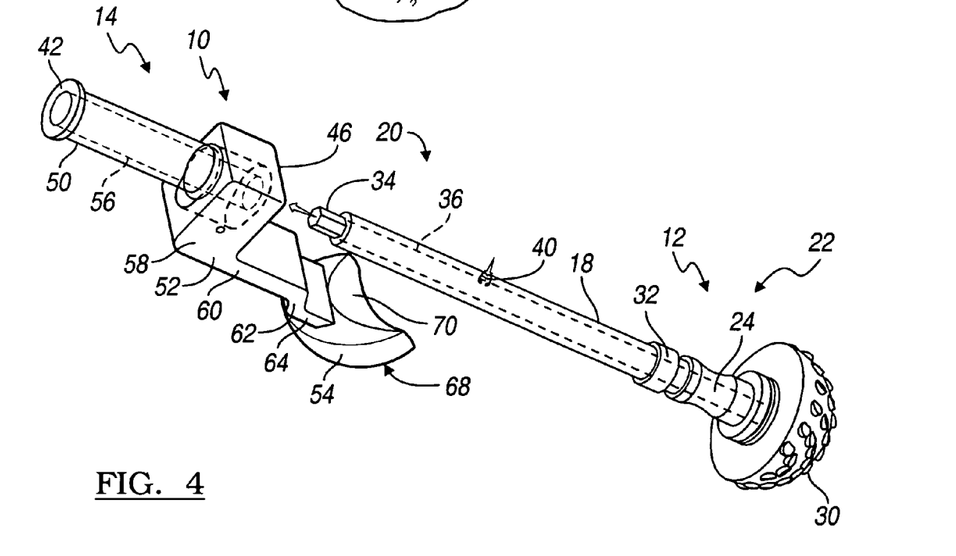
FIG. 4 is an installation view illustrating the reamer guide being assembled onto the reamer.

In one example, the stopper 40 may be moveable between an operating position (FIG. 1) and an assembly position (depressed, as shown in FIG. 4). In the operating position, the stopper 40 may sit proud on the longitudinal shaft 18. In the assembly position, the stopper 40 may be moved to a location substantially flush with the longitudinal shaft 18. In one example, the stopper 40 may be depressed manually such as with a thumb. In this way, the reamer guide 14 may be slidably installed from the proximal end 20 of the longitudinal shaft 18 and slid in a direction toward the cutting head 30 until the proximal surface 42 of the reamer guide 14 passes beyond the stopper 40. Once the reamer guide 14 has sufficiently passed beyond the stopper 40, the stopper 40 may return to the operating position.

According to one example, the stopper 40 may define a pin having a biasing member 44. The biasing member 44 may normally bias the stopper 40 in the operating position. The stopper 40 may be depressed in a direction toward the longitudinal shaft 18 thereby overcoming a bias of the biasing member 44 until the distal surface 46 of the reamer guide 14 passes over the stopper 40. Once the proximal surface 42 of the reamer guide 14 passes completely over the stopper 40, the biasing member 44 may urge the stopper 40 outward and to the operating position. It is appreciated that the configuration of the stopper 40 is merely exemplary and that other arrangements are contemplated. It is further appreciated that the cutting head 30 shown is merely exemplary and that other cutting heads may be used.

Figure 2A:
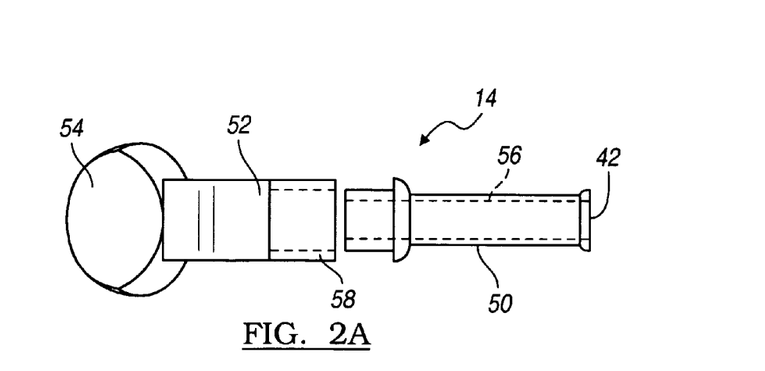
FIG. 2A is a side view of the reamer guide removed from the reamer for illustration.
Figure 2B:
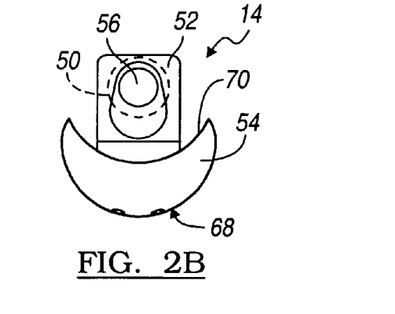
FIG. 2B is an axial view of the reamer guide of FIG. 2A.
Figure 2C:
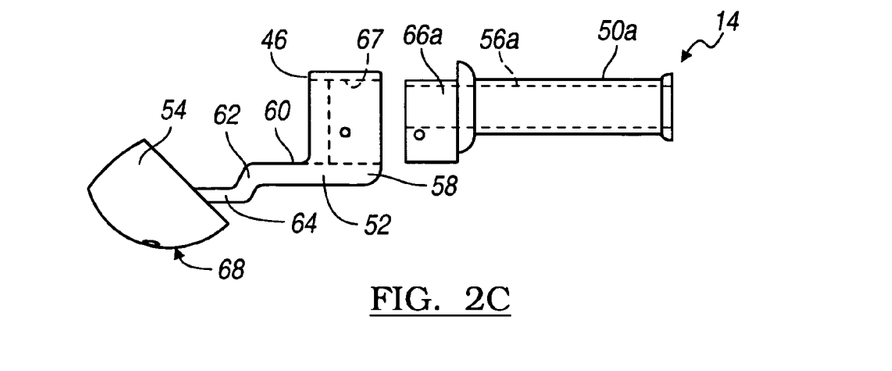
FIGS. 2C and 2D are side views of the reamer guide of FIG. 2A using different body members according to various embodiments.
Figure 2D:
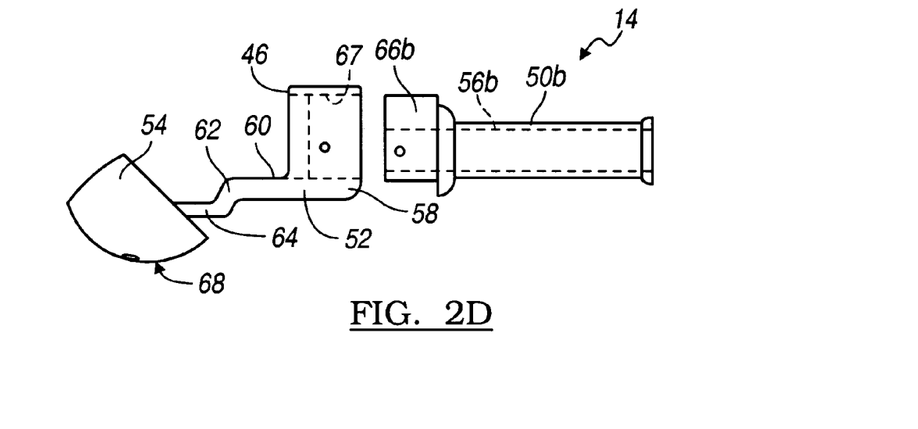
Figure 2E:
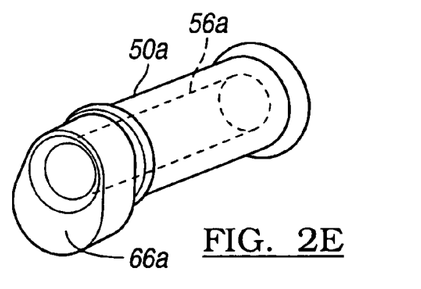
FIGS. 2E and 2F are perspective views of the exemplary body members of FIGS. 2C and 2D for selectively attaching to the reamer guide according to various embodiments.
Figure 2F:
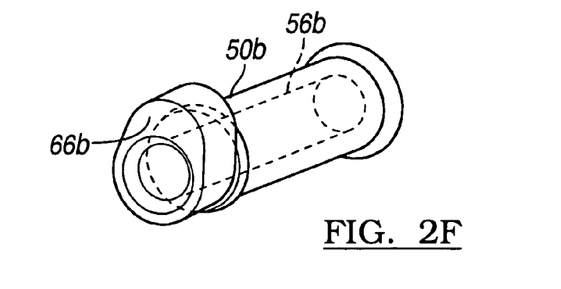
Figure 3:
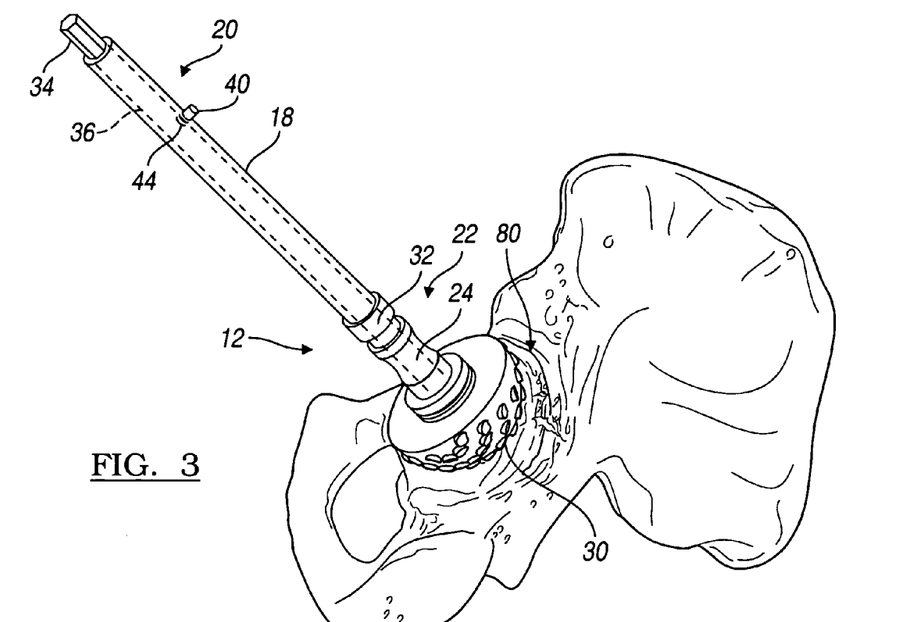
FIG. 3 is a perspective view of the reamer reaming an acetabulum according to an exemplary method of the present teachings.

With reference now to FIGS. 1-2F, the reamer guide 14 will be described in greater detail. The reamer guide 14 may be formed of rigid material such as polyethylene, metal, or other suitable material. The reamer guide 14 generally includes a cannulated body 50, an arm portion 52 and a locator member 54. The cannulated body 50 defines an opening 56. As will be described in greater detail herein, the body 50 may define a handle for a user to grasp during operation. In one example, the reamer guide 14 may be one-piece. A collar 58 is formed at a transition between the body 50 and the arm 52. The collar 58 may extend at a right angle with respect to the body 50. The arm 52 may define a first section 60 arranged parallel to an axis defined by the longitudinal shaft 18, a second section 62 arranged at an angle relative to the axis and a third section 64 arranged parallel to the first section 60. Such a configuration positions the locator member 54 offset relative to the cutting head 30.

With specific reference now to FIGS. 2C-2F, the reamer guide 14 may be adapted to receive various cannulated bodies 50a and 50b. Each cannulated body 50a and 50b defines a male oval insertion portion 66a and 66b, respectively. In general, each male oval insertion portion 66a and 66b defines an oval having a generally trapezoidal shape including a smaller side and a larger side. As shown, the opening 56a of the body 50a is aligned with the smaller side of the insertion portion 66a whereas the opening 56b of the body 50b is aligned with the larger side of the insertion portion 66b. In this way, various lateral offsets may be obtained between the reamer 30 and the locator member 54 depending on the body 50 used. For illustrative purposes, the insertion portion 66a is shown received into a complementary female receiving portion 67 defined on the collar 58 in FIG. 2C. Similarly, the insertion portion 66b is shown received into the complementary female receiving portion 67 in FIG. 2D. As shown, the body 50b will present a larger offset between the reamer 30 and the locator member 54 as compared to the body 50a. As can be appreciated, the trapezoidal oval design requires insertion into the female receiving portion 67 in only one orientation. It is appreciated that the opening 56 may be defined anywhere relative to the insertion portion 66 to provide a variety of desired offsets. Similarly, it is appreciated that other geometries and configurations of the body and collar may be used to allow for various relative offsets.

Figure 11:
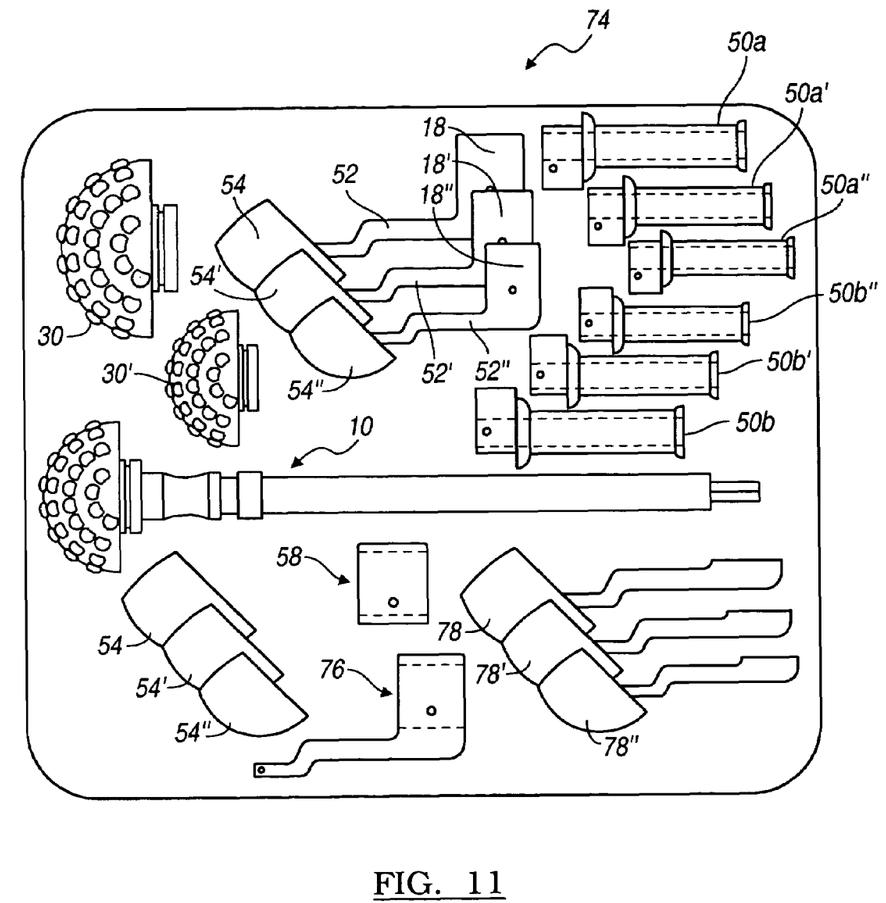
FIG. 11 is a plan view of a kit of reamers, reamer guides, and locator members.

The locator member 54 may define a spherical outer engaging surface 68. The locator member 54 may further define a concave recess 70 for accommodating the cutting head 30 in the assembled position, see e.g. FIGS. 2B and 5. With reference to FIG. 11, a kit 74 of guide members 18, 18', 18" may be provided, each having selected geometrical characteristics. For example, a set of guide members 18, 18', 18" may each define arms 52, 52', 52" extending at various parallel offsets relative to the body 50, 50', 50". In addition, guide members having various locator members 54, 54', 54" may be provided. While specifically shown as one-piece, the guide members 18, 18', 18" may also comprise modular components. In this way, it is contemplated that the body 50, the arm portion 52 and/or the locator member 54 may be separate components. For example, various locator members 54, 54' and 54" may be selectively attached to a handle portion 76. It is contemplated that the locator members 54, 54' and 54" may secure to the handle portion by any suitable means such as a quick connect for example. In other examples, a unitary locator member and arm portion 78, 78' and 78" may be selectively attached to a handle portion 50. As a result, a surgeon may assemble a desired tool having characteristics suitable for a given patient. It is appreciated that the kit 7 may also provide various cutting heads 30, 30'.

With continued reference to FIGS. 1-2F and further reference to FIGS. 3-6 and 9, an exemplary method for using the tool 10 will be described in greater detail. When revision surgery is performed, the primary acetabular cup may be removed. An acetabulum 80 may then be reamed such as with the reamer 12. Initially, a surgeon may determine a suitable cutting member 30, 30' (FIG. 11) for a given patient.

Initially, a driver (not shown) may be operably coupled with the mating structure 34 to impart rotational force through a reamer drive shaft 36 to the cutting head 30. The acetabulum 80 may be generally hemispherically reamed until concentric removal of all acetabular cartilage and/or bone cement is achieved. Once the acetabulum 80 has been appropriately reamed, acetabular trial gauges (not shown), which are well known in the art, may be used to determine and confirm the diameter of the acetabular cup to be used. At this point, a surgeon may access the defect to be reamed and identify which reamer guide 52, 52', 52" (FIG. 11), body 50a-50b", or which handle 76 and locator members 54, 54', 54" to select for achieving the proper reaming area.

Once the acetabulum 80 has been sufficiently prepared, the reamer guide 14 may be slidably inserted onto the longitudinal shaft 18 of the reamer 12. In one example, the driver may be disconnected from the mating structure 34 and the opening 56 of the reamer guide 14 advanced onto the proximal end 20 of the longitudinal shaft 18 (FIG. 4). Next, the reamer guide 14 may be further advanced toward the distal end 22 of the longitudinal shaft 18. In one example, it may be necessary to manually depress the stopper 40 to allow the body 50 of the reamer guide 14 to initially pass over the stopper 40. In another example, the force of the reamer guide 14 may sufficiently depress the stopper 40 concurrently while being advanced into the operating position. While not shown, it is contemplated that the opening 56 may be slightly tapered at the collar 58 to facilitate initial sliding of the reamer guide 14 over the stopper 40. Once the reamer guide 14 passes completely over the stopper 40, the stopper 40 may return to its outward position by way of the biasing member 44.

Figure 5:
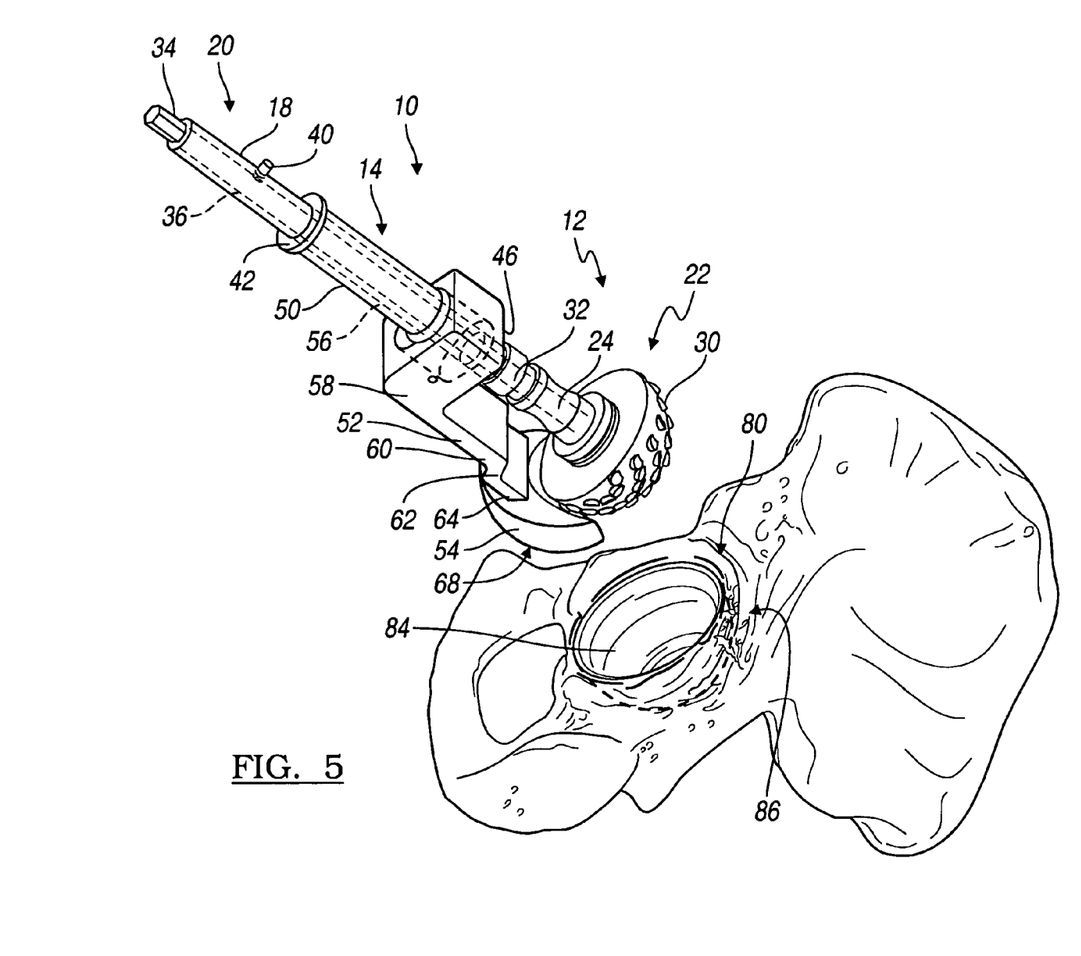
FIG. 5 is a perspective view of an assembled tool approaching an acetabular socket to ream a defect adjacent the socket.
Figure 6:
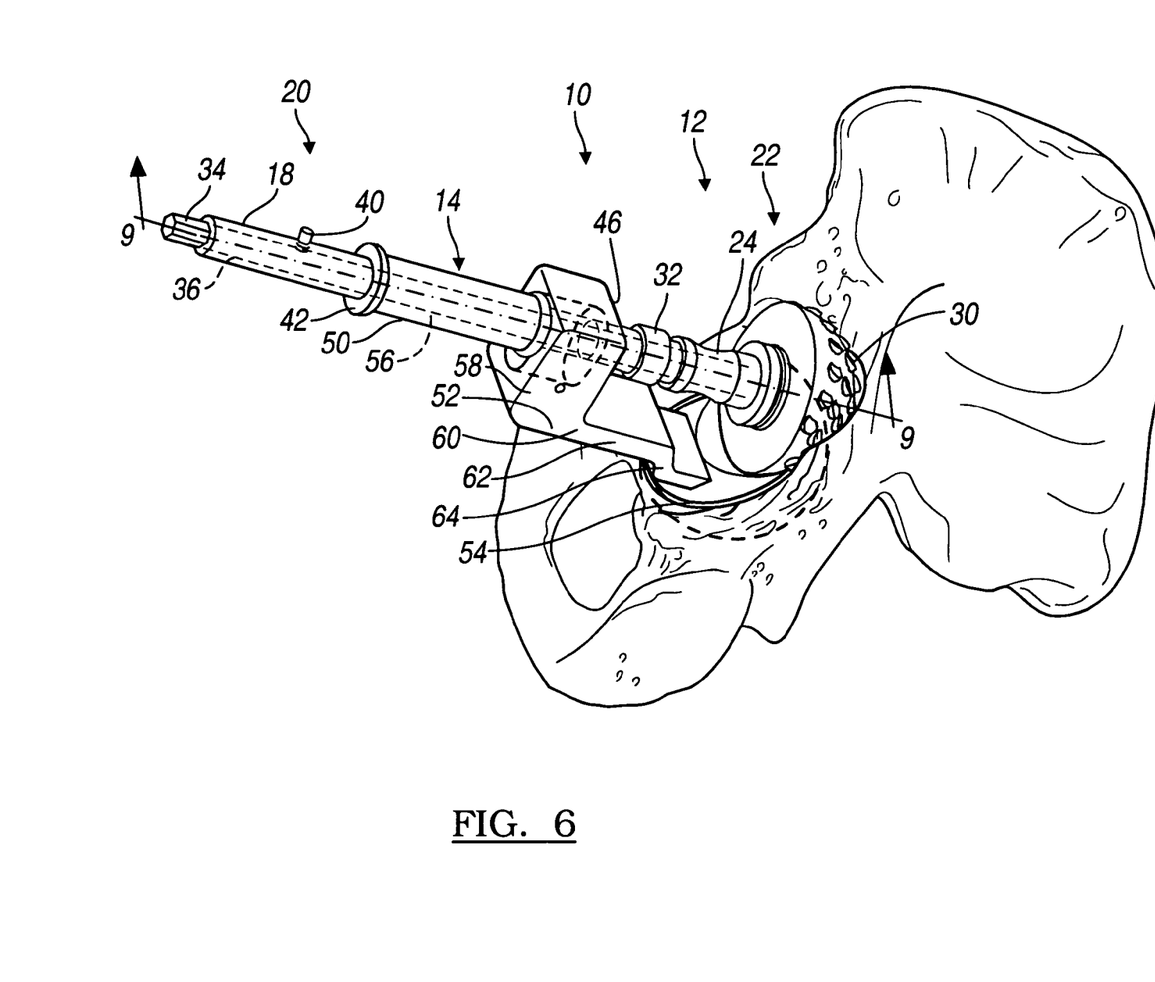
FIG. 6 is a perspective view of a locator member of the reamer guide positioning on the reamer socket while the reamer reams the defect according to the present teachings.

As viewed in FIG. 5, the tool 10 is in the assembled position and ready for use. As described above, in one example, the reamer guide 14 of the tool 10 may be used to positively locate the reamer 12 within a socket 84 of the acetabulum 80 while reaming a defect 86 identified adjacent the socket 84 of the acetabulum. At this point, the locator member 54 may be located in a nested position within the socket 84 of the reamed acetabulum 80 (FIG. 6). It is appreciated that the locator member 54 may be generally located against the socket 84 at a location opposite of the defect 86. Once the locator member 54 is in a secure position within the socket 84, the defect 86 may be reamed. In one example, a surgeon may grasp the body 50 of the guide member 14 with one hand and grasp the longitudinal shaft 18 of the reamer 12 with the other hand. The surgeon may advance the longitudinal shaft 18 of the reamer 12 through the opening 56 of the reamer guide 14. According to one example, translation of the reamer 12 may be limited between the stopper 40 and the hub 32. It is appreciated that various reamer guides 14 may be provided that each define a specific length. As a result, a surgeon may preselect a reamer guide 14 that limits a reaming depth to a specified distance according to a given patient. In one example, the stopper 40 may be located in a position to preclude the reamer 30 from attaining a parallel relationship with the locator member 54. Explained differently, translation of the reamer 30 along its axis may be limited to a location wherein a plane defined at the tip of the reamer 30 normal to the drive shaft 36 intersects the locator member 54.

Figure 7:
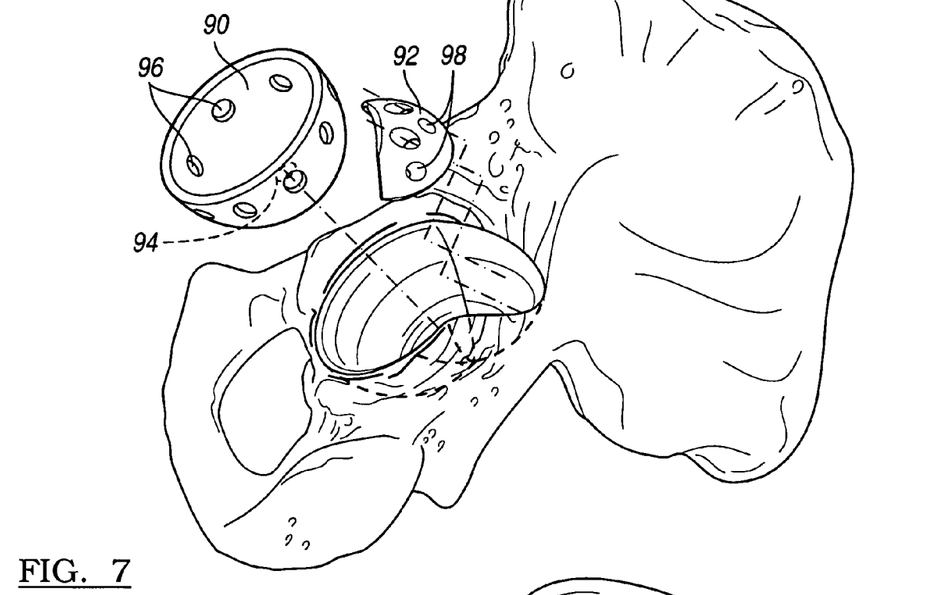
FIG. 7 is a perspective view of an exemplary acetabular cup and augment ready to be implanted at the implant site.
Figure 8:
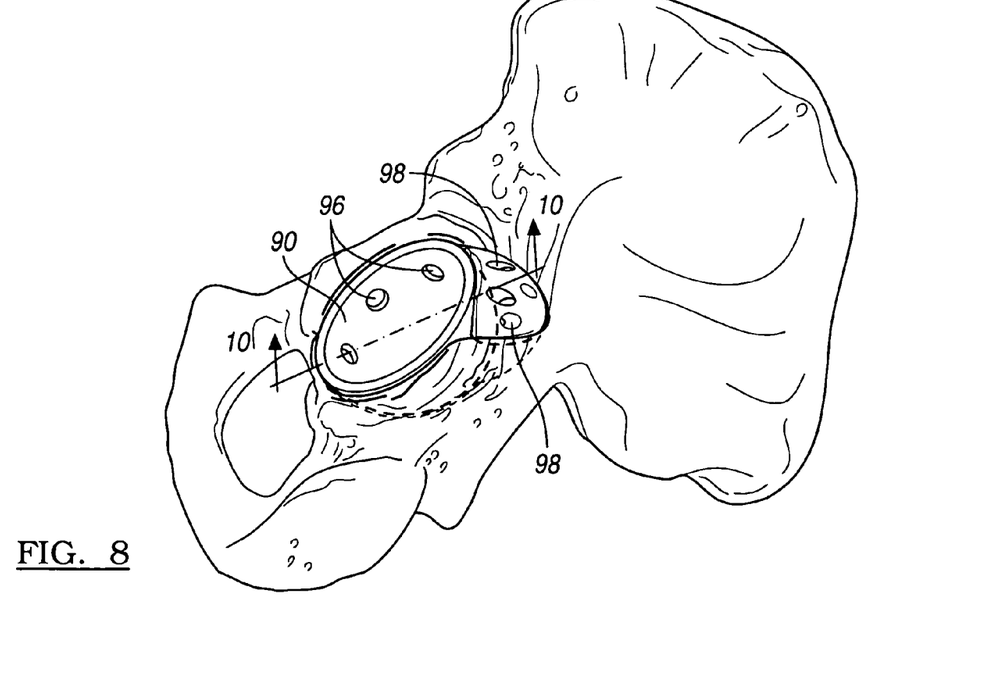
FIG. 8 is a perspective view of the exemplary acetabular cup and augment shown in an implanted position.
Figure 9:
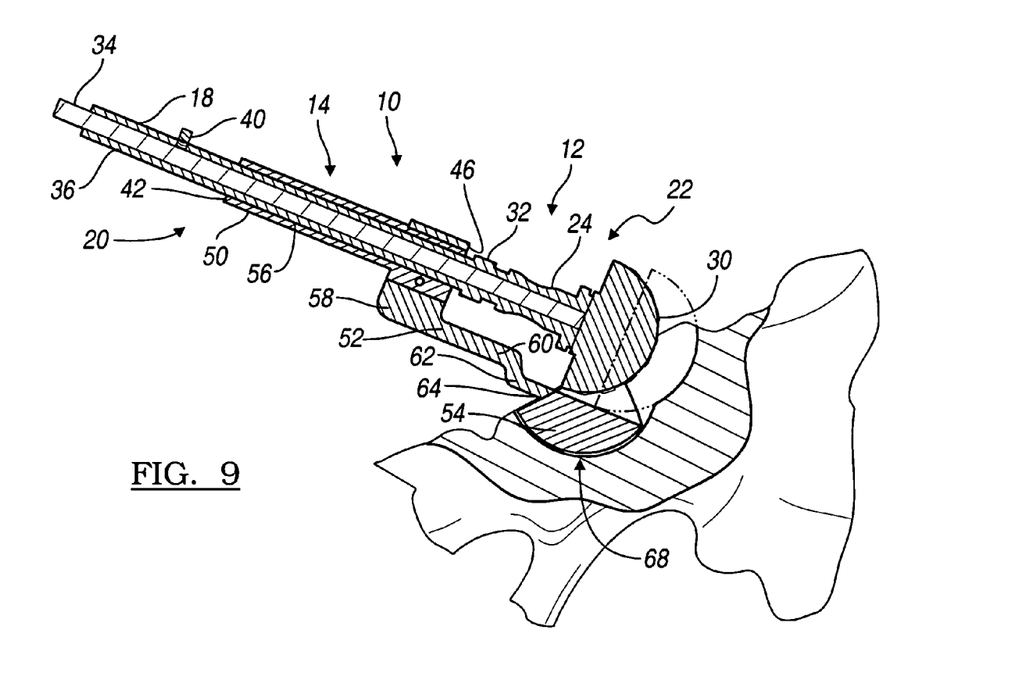
FIG. 9 is a sectional view of the tool during reaming taken along line 9-9 of FIG. 6.
Figure 10:
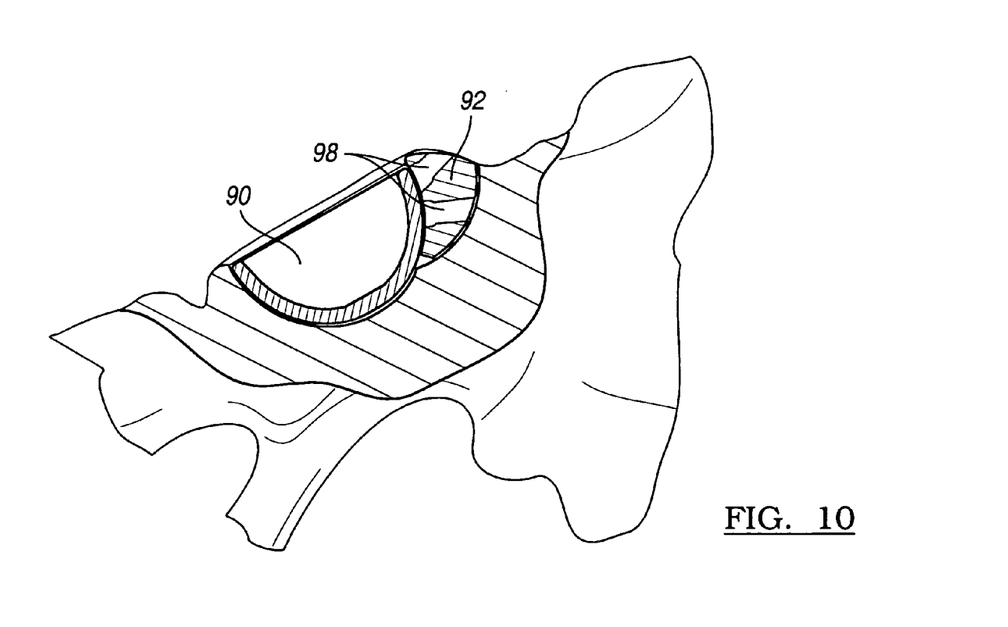
FIG. 10 is a sectional view of the acetabular cup and augment taken along line 10-10 of FIG. 8.

Turning now to FIGS. 7 and 8, an acetabular cup 90 and augment 92 may be implanted. Exemplary acetabular cups and augments may be found in co-pending application, U.S. Ser. No. 11/357,868, filed Feb. 17, 2006, entitled "Method and Apparatus for use of Porous Implants" also assigned to Biomet, Inc., of Warsaw Ind., which is incorporated herein by reference. In one example, the cup 90 may be impanted at the socket 84 and the augment 92 may be implanted at the reamed defect site. The cup 90 and augment 92 may be implanted by any suitable method. According to one such method, an impacting instrument (not shown) may be used to properly position the acetabular cup 90. In one example, the impacting instrument may be threadably secured to an apical hole 94 of the acetabular cup. Once the orientation of the acetabular cup 90 is acceptable, the inserting instrument may be solidly impacted to fully seat the acetabular cup 90, such that firm rim fixation is achieved. Once the acetabular cup 90 has been solidly impacted, the inserting instrument may be carefully removed from the cup 90.

A plurality of bone screw holes (not specifically shown) may be bored through holes 96 in the acetabular cup 90. Once fixation holes have been formed in the acetabulum 80, a depth gauge, as is also known in the art, may be used to determine the length of the fixation screws. With the length of the screws determined, a fixation screw or multiple screws (not shown) may be inserted into screw holes 96. Fixation screws (not shown) may be similarly used though bores 98 in the augment 92 to secure the augment.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A tool for reaming a cavity in bone comprising:
   a longitudinal shaft having a distal end and a proximal end, said longitudinal shaft extending along a first axis;
   a cutting tool selectively attachable to said distal end opposite said proximal end;
   a guide having a body that defines a second axis through an elongated opening, the guide including a unitarily formed locator member extending therefrom, wherein said locator member includes a spherical outer engaging surface and defines a concave recess on an inner surface that accommodates said cutting tool, said locator member being engageable to a first portion of the bone providing a reference point relative to said cutting tool while said cutting tool engages a second portion of the bone during cutting;
   an arm operably connected between said body and said locator member, said arm having a first section that extends along a third axis that is parallel to and offset from said first axis; and
   wherein said body is slidably advanced onto said longitudinal shaft through said opening from said proximal end to an operating location intermediate said distal end and said proximal end in an assembled position, said first and second axes being collinear.

2. The tool of claim 1 wherein during operation said body provides a gripping portion for a user that is concentric with said longitudinal shaft.

3. The tool of claim 2 wherein said arm further includes a second section positioned intermediate said first section and said locating member and arranged at an angle relative to said first axis.

4. The tool of claim 3 wherein said arm includes a third section operatively coupled between said locator member and said second section, said third section extending along a fourth axis that is parallel to and offset from said third axis.

5. The tool of claim 3 wherein said arm includes a third section operatively coupled between said locator member and said second section, said third section extending along a fourth axis that is parallel to and offset from said third axis.

6. The tool of claim 1 wherein said longitudinal shaft includes a stop member arranged thereon, said stop member moveable between an install position wherein said opening of said guide slidably passes entirely over said stop member and an operating position wherein said guide is precluded from advancing beyond said stop member.

7. The tool of claim 6 wherein said stop member is moved to a position that is substantially flush with said longitudinal shaft in said install position.

8. The tool of claim 6 wherein said stop member comprises a spring biased pin.

9. The tool of claim 8 wherein said longitudinal shaft is selectively translatable through said opening of said body in the operating position, said stop member engaging said guide.

10. A tool for reaming a cavity in bone comprising:
a longitudinal shaft having a distal end and a proximal end, said longitudinal shaft extending alone a first axis;
a stop member extending from a first location on said longitudinal shaft;
a hub extending from a second location on said longitudinal shaft, wherein a first distance is defined between said first and second locations;
a cutting tool selectively attachable to said distal end;
a guide having a body that defines a second axis through an elongated opening, the guide including a locator member extending therefrom, wherein said locator member includes a spherical outer engaging surface and defines a concave recess on an inner surface that accommodates said cutting tool, said locator member being engageable to a first portion of the bone while said cutting tool engages a second portion of the bone during cutting;
an arm operably connected between said body and said locating member, said arm having a first section that extends along a third axis that is parallel to and offset from said first and second axes; and
wherein said guide is movable along said longitudinal shaft between said hub and said stop member, wherein said guide includes a handle concentric with said longitudinal shaft, said handle having an elongated grasping portion that extends a second distance along said longitudinal shaft, said second distance being at least half of said first distance.

11. The tool of claim 10 wherein said arm further includes a second section positioned intermediate said first section and said locating member and arranged at an angle relative to said first axis.

12. The tool of claim 11 wherein said arm includes a third section operatively coupled between said locator member and said second section, said third section extending along a fourth axis that is parallel to and offset from said third axis.

13. The tool of claim 11, further comprising a set of locator members selectively attachable to said arm.

14. The tool of claim 11, further comprising a set of integrally formed locator members and arms selectively attachable to said body.

15. The tool of claim 10 wherein said longitudinal shaft includes a stop member arranged thereon, said stop member moveable between an install position wherein said opening of said guide slidably passes entirely over said stop member and an operating position wherein said guide is precluded from advancing beyond said stop member.

16. The tool of claim 15 wherein said stop member is moved to a position that is substantially flush with said longitudinal shaft in said install position.

17. The tool of claim 15 wherein said stop member comprises a spring biased pin.

18. The tool of claim 17 wherein said longitudinal shaft is selectively translatable through said opening of said body in the operating position, said stop member engaging said guide.

19. The tool of claim 10 wherein said body includes a first and a second body defining a first and a second opening, respectively, for receiving said longitudinal shaft, wherein said first body is selectively attached to said guide such that said longitudinal shaft defines a first offset relative to said locator member and wherein said second body is selectively attached to said guide such that said longitudinal shaft defines a second offset relative to said locator member, wherein said first and second offsets are distinct.

20. A tool for reaming a cavity in bone comprising:
a longitudinal shaft having a distal end and a proximal end, said longitudinal shaft extending alone a first axis;
a cutting tool selectively attachable to said distal end;
a stop member extending from said longitudinal shaft;
a guide having a body that defines a second axis through an elongated opening, the guide including a unitarily formed locator member extending therefrom, wherein said locator member includes a spherical outer engaging surface and defines a concave recess on an inner surface that accommodates said cutting tool, said locator member being engageable to a first portion of the bone providing a reference point relative to said cutting tool while said cutting tool engages a second portion of the bone during cutting;
an arm operably connected between said body and said locator member, said arm having a first section that extends along a third axis that is parallel to and offset from said first and second axes; and
wherein said body is slidably advanced onto said longitudinal shaft through said opening from said proximal end to an operating location in an assembled position and wherein during advancement of said body, said stop member moves to a depressed location relative to said longitudinal member such that an inner diameter defined by said opening accommodates said longitudinal shaft and said stop member while said body advances over said stop member to said operating position.

* * * * *